United States Patent [19]

Payne et al.

[11] 4,411,913
[45] Oct. 25, 1983

[54] 8'-[(3-AMINO-2-HYDROXY-PROPOXY)]-SPIRO-[CYCLOPENTANE-1,2'(1'H)-(3'H)NAPHTALEN]-4'(3'H)-ONES

[75] Inventors: Trevor G. Payne, Arlesheim; Richard Berthold, Bottmingen, both of Switzerland

[73] Assignee: Sandoz Ltd., Basel, Switzerland

[21] Appl. No.: 17,476

[22] Filed: Mar. 5, 1979

Related U.S. Application Data

[63] Continuation of Ser. No. 890,656, Mar. 20, 1978, abandoned.

[30] Foreign Application Priority Data

Jan. 17, 1979 [CH] Switzerland .................... 445/79

[51] Int. Cl.³ ............................................. A01N 33/02
[52] U.S. Cl. ............................... 424/330; 260/465 E; 260/501.18; 424/304; 424/316; 564/304; 564/349
[58] Field of Search ............ 260/465 E, 501.18, 570.7; 424/316, 330, 304

[56] References Cited

U.S. PATENT DOCUMENTS

| | | | |
|---|---|---|---|
| 3,419,560 | 12/1968 | Bernstein et al. | 260/570.8 X |
| 3,641,152 | 2/1972 | Shavel, Jr. et al. | 260/570.7 |
| 3,706,756 | 12/1972 | Werner | 260/570.8 X |
| 4,034,041 | 7/1977 | Freed et al. | 260/571 |
| 4,172,093 | 10/1979 | Dahlander et al. | 260/570.8 |

Primary Examiner—Robert V. Hines
Attorney, Agent, or Firm—Gerald D. Sharkin; Robert S. Honor; Thomas O. McGovern

[57] ABSTRACT

Compounds of of formula I

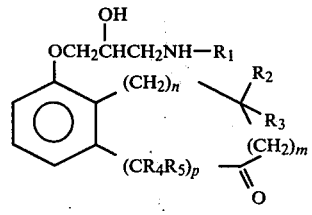

wherein
(i) m is O, n is 2 and p is 1 or
(ii) m is 0 or 1, n is 1, and p is 1 or
(iii) m is 1, n is 1 or 2 and p is 0,
$R_1$ is (i) alkyl of 3 to 7 carbon atoms or (ii) phenylalkyl, phenoxyalkyl or phenylthioalkyl of 8 to 11 carbon atoms in the aggregate thereof and wherein the phenyl ring is separated by at least 2 carbon atoms from the nitrogen atom to which $R_1$ is bound and wherein the phenyl ring is unsubstituted, or monosubstituted by, or independently disubstituted by, alkyl or alkoxy of 1 to 4 carbon atoms, halogen of atomic number from 9 to 35, trifluoromethyl or cyano,
$R_2$ and $R_3$ are either together straight chain alkylene of 4 to 6 carbon atoms, or, independently, hydrogen or alkyl of 1 to 4 carbon atoms, with the proviso that when m is 1, n is 1 and p is 0 then at least one of $R_2$ and $R_3$ is other than hydrogen, and
$R_4$ and $R_5$ are, independently, hydrogen or alkyl of 1 to 4 carbon atoms,
are useful in the treatment of coronary disorders.

10 Claims, No Drawings

8'-[(3-AMINO-2-HYDROXY-PROPOXY)]-SPIRO-[CYCLOPENTANE-1,2'(1'H)-(3'H)NAPHTALEN]-4'(3'H)-ONES

This is a continuation-in-part of our copending application Ser. No. 890,656, filed Mar. 20, 1978 and now abandoned.

The present invention relates to 1-amino-3-aryloxy-2-propanols.

The present invention provides compounds of formula I

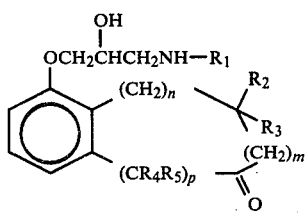

wherein
(i) m is 0, n is 2 and p is 1 or
(ii) m is 0 or 1, n is 1, and p is 1 or
(iii) m is 1, n is 1 or 2 and p is 0, $R_1$ is (i) alkyl of 3 to 7 carbon atoms or (ii) phenylalkyl, phenoxyalkyl or phenylthioalkyl of 8 to 11 carbon atoms in the aggregate thereof and wherein the phenyl ring is separated by at least 2 carbon atoms from the nitrogen atom to which $R_1$ is bound and wherein the phenyl ring is unsubstituted, or mono-substituted by, or independently disubstituted by, alkyl or alkoxy of 1 to 4 carbon atoms, halogen of atomic number from 9 to 35, trifluoromethyl or cyano, $R_2$ and $R_3$ are either together straight chain alkylene of 4 to 6 carbon atoms, or, independently, hydrogen or alkyl of 1 to 4 carbon atoms, with the proviso that when m is 1, n is 1 and p is 0 then at least one of $R_2$ and $R_3$ is other than hydrogen, and $R_4$ and $R_5$ are, independently, hydrogen or alkyl of 1 to 4 carbon atoms.

When m is 0, preferably n is 2 and p is 1. When m is 1, preferably n is 1. Alkyl and/or alkoxy contains preferably 1 or 2 carbon atoms, especially 1 carbon atom, except where otherwise stated hereinafter. Halogen is preferably chlorine or bromine, especially chlorine. Alkylene contains preferably 4 or 5 carbon atoms, especially 4 carbon atoms.

The alkylene moiety of the phenylalkyl, phenoxyalkyl or phenylthioalkyl radical has preferably 2 to 4 carbon atoms. When the alkylene moiety contains more than 2 carbon atoms it is preferably branched, preferably in the α-position to the nitrogen atom to which $R_1$ is bound. When the phenyl ring is mono-substituted, the substituent is preferably in the 3 or 4 position. When the phenyl ring is disubstituted, the substituents are preferably in the 3 and 4 positions and are preferably identical.

When $R_1$ is alkyl, this moiety preferably has 3 to 5 carbon atoms, especially 3 or 4 carbon atoms. This is preferably branched, especially in the α-position.

$R_1$ is preferably alkyl or phenylalkyl, especially alkyl. $R_2$ and $R_3$ are preferably either each alkyl or together alkylene. $R_4$ and $R_5$ are preferably each hydrogen.

The present invention provides a process for the production of a compound of formula I as defined above which comprises reacting a compound of formula II

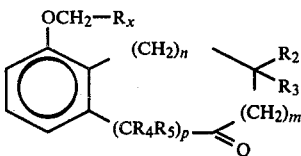

wherein
m, n, p and $R_2$ to $R_5$ are as defined above, and
$R_x$ is a group capable of reacting with an amine to give a 2-amino-1-hydroxyethyl group,
with a compound of formula III $$R_1NH_2 \qquad III$$

wherein $R_1$ is defined above.

The present process is an amination by a primary amine. It may be effected in conventional manner for the production of analogous 3-amino-2-hydroxypropoxyaryl compounds. For example $R_x$ may be a group of formula

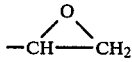

or a reactive derivative of this group, e.g. of formula —CH(OH)—CH$_2$Y wherein Y is halogen, preferably chlorine or bromine, or a group $R_y$—SO$_2$—O— wherein $R_y$ is phenyl, tolyl or lower alkyl. Y is especially chlorine.

The reaction is effected preferably in an inert organic solvent, e.g. in an appropriate ether such as dioxane. Optionally an excess of a compound of formula III may be used as solvent. Alternatively the reaction may be effected in a fusion melt.

Suitable reaction temperatures may be from about 20° to about 200° C., conveniently the reflux temperature of the reaction mixture when a solvent is present.

Free base forms of the compounds of formula I may be converted into acid addition salt forms in conventional manner and vice versa. Suitable acids for salt formation include maleic acid, tartaric acid and fumaric acid.

In the compounds of formula I, the carbon atom to which the hydroxy group is bound is asymmetrically substituted. The compounds may thus exist in the racemic form or in individual optical isomer form. If either $R_2$ and $R_3$ or $R_4$ and $R_5$ are not identical, then the compounds may exist in individual diastereoisomeric forms. In certain conditions these diastereoisomeric forms may be interconverted, e.g. when there is a hydrogen atom attached to a carbon atom adjacent to a carbonyl group, epimerisation may occur in the presence of a base. Preferred compounds are, however, the compounds wherein $R_2$ and $R_3$ are identical and $R_4$ and $R_5$ are identical. The preferred optical isomer has the S configuration at the asymmetrically substituted carbon atom of the hydroxypropoxy side chain.

Individual optical isomer forms and diastereoisomeric forms may be obtained in conventional manner. For example the S isomers may be produced by using optically active starting materials or by fractional crystallisation using optically active acids, e.g. as described in German Offenlegungsschrift (DOS) No. 28 10 732.

Individual diastereoisomeric forms may be similarly obtained using fractional crystallisation, or chromatography, of a mixture of salt forms or using optically active starting materials.

The starting materials may be obtained as follows:

Compounds of formula II may be obtained by demethylating or debenzylating a compound of formula IV

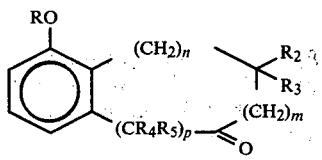

IV wherein m, n, p and $R_2$ to $R_5$ are as defined above, and

R is methyl or benzyl, and replacing the hydroxy group by a group —O—CH$_2$—R$_x$ in the resulting phenol in known manner.

A compound of formula IVa

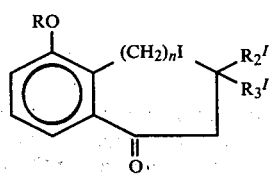

IVa wherein $n^I$ is 1 or 2,

R is as defined above, and either $R_2^I$ and $R_3^I$ together are straight chain alkylene of 4 to 6 carbon atoms, or $R_2^I$ and $R_3^I$ are, independently, hydrogen or alkyl (C$_{1-4}$) with the proviso that, when $n^I$ is 2, $R_2^I$ and $R_3^I$ are not both hydrogen, may be obtained by (a) reacting a compound of formula V

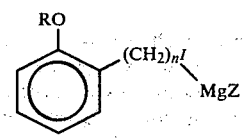

V wherein $n^I$ and R are as defined above, and

Z is chlorine or bromine, with a compound of formula VI

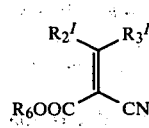

VI wherein $R_2^I$ and $R_3^I$ are as defined above and $R_6$ is alkyl (C$_{1-4}$), to produce a compound of formula VII

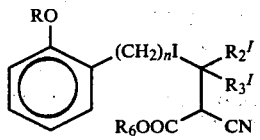

VII (b) hydrolysing the compound of formula VII and splitting off carbon dioxide from the reaction product to produce a compound of formula VIII

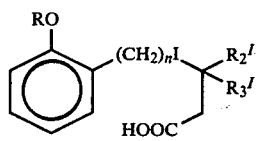

VIII and, (c) cyclizing the resulting compound of formula VIII with e.g. poly-phosphoric acid.

For the production of a compound of formula VIII when $n^I$ is 1 and $R_2$ and $R_3$ are both hydrogen, it is preferred to react cyanoethylene with a compound of formula V and to hydrolyse the resulting compound.

Compounds of formula IVaa

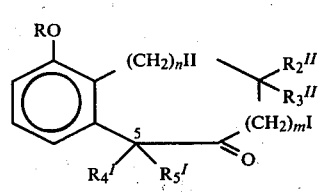

IVaa may be produced by oxidizing the corresponding benzo-5-suberol with, for example, chromium trioxide or manganese dioxide.

Compounds of formula IVb

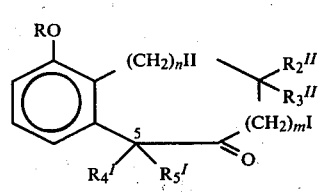

IVb wherein either $m^I$ is 0 or 1 and $n^{II}$ is 1, or $m^I$ is 0 and $n^{II}$ is 2, R is as defined above, and either $R_2^{II}$ and $R_3^{II}$ together are straight-chain alkylene (C$_{4-6}$), or $R_2^{II}$ and $R_3^{II}$ are, independently, hydrogen or alkyl (C$_{1-4}$), $R_4^I$ and $R_5^I$ are, independently, alkyl (C$_{1-4}$), may be obtained by alkylating the corresponding 5-non-alkylated compounds.

Compounds of formula IVc

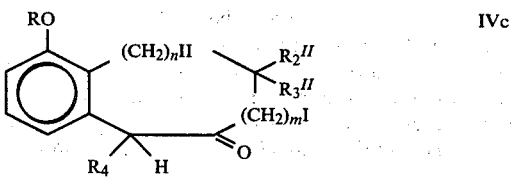

wherein $m^I$, $n^{II}$, $R_1$, $R_2^{II}$, $R_3^{II}$ and $R_4$ are as defined above, may be obtained by (a) effecting a Wittig reaction between a compound of formula IVd

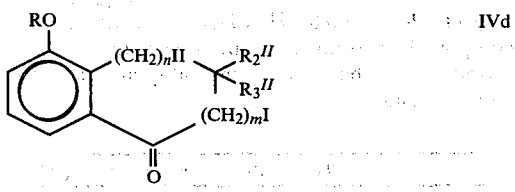

with a compound of formula IX

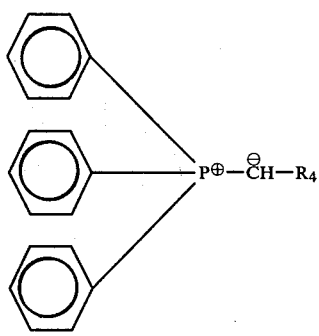

to obtain a compound of formula X

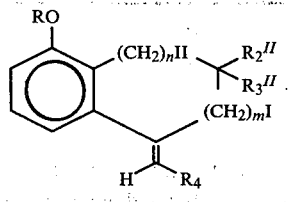

and, (b) reacting the resultant compound of formula X with thallium trinitrate in the presence of a lower alkanol.

When $m^I$ is 0 and $R_2^{II}$ and $R_3^{II}$ are both other than hydrogen in the compound of formula X, this may alternatively be produced by (a) reacting the appropriate compound of formula IVd with a Grignard reagent of an alkyl bromide to produce a carbinol and (b) splitting off water from the resulting carbinol. Compounds of formula IVda

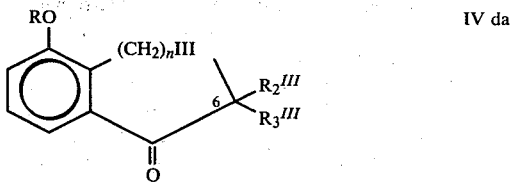

wherein
$n^{III}$ is 1 or 2,
R is defined above, and
either $R_2^{III}$ and $R_3^{III}$ together are straight chain alkylene ($C_{4-6}$), or
$R_2^{III}$ is hydrogen or alkyl ($C_{1-4}$), and
$R_3^{III}$ is alkyl ($C_{1-4}$), may be produced by mono-or di-alkylating the corresponding compound wherein the 6 position is unsubstituted.

In so far the preparation of any particular starting material is not particularly described, this may be effected in conventional manner.

In the following examples all temperatures are in degrees Centigrade and are uncorrected.

EXAMPLE 1

1-(3-tert-butylamino-2-hydroxypropoxy)-6,7,8,9-tetrahydro-7,7-dimethyl-5H-benzocyclohepten-6-one 2,2 g crude 1-(3-chloro-2-hydroxypropoxy)-6,7,8,9-tetrahydro-7,7-dimethyl-5H-benzocyclohepten-6-one in 20 ml dioxane and 10 ml tert-butylamine are heated at 130° for 20 hours in an autoclave. The reaction mixture is divided between 10% (w/w) aqueous tartaric acid solution and ether. The aqueous phase is made alkaline and extracted with ether. Evaporation of the ether phase yields the title compound (M.pt of hydrogen maleate 186°-188° after crystallization from ethanol).

The starting material may be obtained as follows:

(a) 44.0 g 5-methoxy-1-tetralone in tetrahydrofuran are added dropwise to a suspension of 21 g sodium hydride in tetrahydrofuran. 142 g methyl iodide in tetrahydrofuran is added to the resulting mixture. 5-methoxy-2,2-dimethyl-1-tetralone (B.pt 162°-170°/12 mm) is obtained after working up.

(b) A solution of methyl magnesium iodide (produced from 69.7 g methyl iodide and 11.9 g magnesium turnings in ether) is treated with a solution of 66.5 g 5-methoxy-2,2-dimethyl-1-tetralone in ether. The reaction mixture is treated with a solution of 62 g ammonium chloride in water. The resultant carbinol is extracted with ether and is treated, dissolved in benzone, with 0.5 g para-toluene-sulphonic acid. After chromatographic purification on basic aluminum oxide using petroleum ether as eluant, methyl 1-(5,6,7,8-tetrahydro-6,6-dimethyl-5-methylene-naphthyl) ether is obtained as an oil which is worked up further directly.

(c) 125 g thallium trinitrate trihydrate in methanol are treated with 55 g methyl 1-(5,6,7,8-tetrahydro-6,6-dimethyl-5-methylene-naphthyl) ether in benzene. The precipitated thallium nitrate is filtered off and the solution is extracted with methylene chloride. The resultant 6,7,8,9-tetrahydro-1-methoxy-7,7-dimethyl-5H-benzolcyclohepten-6-one melts at 58°-59° (from hexane).

(d) 4.0 g 6,7,8,9-tetrahydro-1-methoxy-7,7-dimethyl-5H-benzocyclohepten-6-one are refluxed with 45 ml acetic acid and 5 ml 48% hydrochloric acid for 20 hours. The solution is concentrated, diluted with water and extracted with ether. After removal of the ether, 6,7,8,9-tetrahydro-7,7-dimethyl-6-oxo-5H-benzocycloheptan-1-ol melts at 152°–154° (from toluene).

(e) Two drops of piperidine are added to 1.8 g 6,7,8,9-tetrahydro-7,7-dimethyl-6-oxo-5H-benzocyclohepten-1-ol in 8 ml epichlorohydrin. The mixture is stirred at 100° for 4 hours. The solution is evaporated, taken up in ether, filtered and concentrated to give crude 1-(3-chloro-2-hydroxypropoxy)-6,7,8,9-tetrahydro-7,7-dimethyl-5H-benzocyclohepten-6-one.

EXAMPLE 2

8'-(3-tert-butylamino-2-hydroxypropoxy)spiro [cyclolpentane-1,2'(1'H)-naphthalen]-4'(3'H)-one The title compound is obtained in analogous manner to Example 1 starting from 8'-(3-chloro-2-hydroxypropoxy)spiro[cyclopentane-1,2'(1'H)-naphthalen]-4'(3'H)-one. M.pt. (hydrogen maleate) 188°–190° (from ethanol).

The starting material may be obtained as follows:

(a) A solution of 39.9 g cyclopentylidene cyanoacetic acid ethyl ester in 350 ml tetrahydrofuran is added dropwise to a solution of 2-methoxybenzyl magnesium chloride (produced from 5.3 g magnesium and 31.2 g 2-methoxybenzyl chloride in 400 ml ether). The mixture is stirred for 2 hours at room temperature. The mixture is treated with a 300 ml 15% ammonium chloride solution. The product is extracted with ether and the ethereal solution concentrated to yield crude α-cyano-[1-(2-methoxybenzyl)cyclopentane]-acetic acid ethyl ester which distilled at 140°–180°/0.002 mm Hg.

(b) 33.6 g potassium hydroxide are added to a solution of 32.4 g α-cyano-[1-(2-methoxybenzyl)cyclopentane]-acetic acid ethyl ester in 300 ml ethylene glycol. The mixture is stirred at 180° for 40 hours. The solution is cooled, poured onto ice/water and the neutral side products removed by extraction with ether. The aqueous phase is made acid with hydrochloric acid and extracted with ether. After removal of the solvent 1-(2-methoxybenzyl)cyclopentane acetic acid (M.pt 85°–87° from hexane) is obtained.

(c) 5.7 g 1-(2-methoxybenzyl)cyclopentane-acetic acid is added with stirring to 30 g polyphosphoric acid at 110°. The mixture is cooled and treated with 250 ml water. After extraction with ether and concentration of the ether extract 8'-methoxy-spiro[cyclopentane-1,2'(1'H)-naphthalen]-4'(3'H)-one (M.pt 62°–66°) is obtained.

(d) In analogous manner to Example 1 step (d), 8'-hydroxy-spiro[cyclopentane-1,2'(1'H)-naphthalen]-4'(3'H)-one (M.pt 163°–165° from toluene) is obtained from the 8-methoxy derivative, and is converted into crude 8'-(3-chloro-2-hydroxypropoxy)-spiro[cyclopentane-1,2'(1'H)-naphthalen]-4'(3'H)-one in analogous manner to Example 1 step (e).

From the appropriate compound of formula II wherein $R_x$ is $CH(OH).CH_2Cl$ and the appropriate compound of formula III the following compounds of formula I may be obtained in analogous manner to Examples 1 and 2:

| Ex. No. | $R_1$ | $R_2$ | $R_3$ | $R_4$ | $R_5$ | m | n | p | M.Pt (1) |
|---|---|---|---|---|---|---|---|---|---|
| 3 | $-C(CH_3)_3$ | $-(CH_2)_5-$ | | — | — | 1 | 1 | 0 | (2) 119–121° |
| 4 | $-C(CH_3)_3$ | $-CH_3$ | $-CH_3$ | — | — | 1 | 2 | 0 | (3) 152–154° |
| 5 | $-C(CH_3)_3$ | $-CH_3$ | $-CH_3$ | — | — | 1 | 1 | 0 | (3) 194–196° |
| 6 | $-C(CH_3)_2-CH_2O-C_6H_4-CN$ | $-CH_3$ | $-CH_3$ | — | — | 1 | 1 | 0 | (3) 150–152° |
| 7 | $-C(CH_3)_3$ | $-C_2H_5$ | $-C_2H_5$ | — | — | 1 | 1 | 0 | 208–210° |
| 8 | $-C(CH_3)_3$ | $-H$ | $-H$ | — | — | 1 | 2 | 0 | 212–216° |
| 9 | $-C(CH_3)_2-CH_2O-C_6H_4-CF_4$ | $-CH_3$ | $-CH_3$ | — | — | 1 | 1 | 0 | 173–175° |
| 10 | $-C(CH_3)_3$ | $-CH(CH_3)_2$ | $-H$ | — | — | 1 | 1 | 0 | (4) 215–217° |
| 11 | $-C(CH_3)_3$ | $-CH_3$ | $-CH_3$ | $-H$ | $-H$ | 0 | 1 | 1 | 205–208° |
| 12 | $-C(CH_3)_3$ | $-CH_3$ | $-CH_3$ | $-H$ | $-H$ | 1 | 1 | 1 | 211–213° |
| 13 | $-C(CH_3)_3$ | $-H$ | $-H$ | $-CH_2$ | $-CH_3$ | 1 | 1 | 1 | 206–208° |
| 14 | $-C(CH_3)_3$ | $-H$ | $-H$ | $-H$ | $-H$ | 1 | 1 | 1 | 203–205° |
| 15 | $-C(CH_3)_3$ | $-H$ | $-H$ | $-CH_3$ | $-CH_3$ | 0 | 1 | 1 | (2) 130–132° |
| 16 | $-C(CH_3)_3$ | $-CH_3$ | $-CH_3$ | $-CH_3$ | $-CH_3$ | 0 | 2 | 1 | 210–212° |

(1) Melting point of bis [base] fumarate unless otherwise stated
(2) free base form
(3) hydrogen maleate
(4) 1:1 diastereoisomeric mixture In analogous manner to Example 1 the following compounds of formula I are obtained wherein m=1, n=1 and p=0, $R_2$ and $R_3$ are each n-butyl and $R_1$ is:

(a) 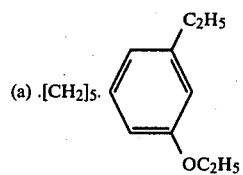 .[CH₂]₅.

(b) 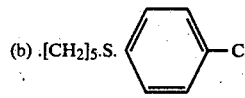 .[CH₂]₅.S.

(c) .[CH$_2$]$_5$.S—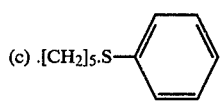

EXAMPLE 17

8'-[(2S)-3-tert-butylamino-2-hydroxypropoxy]spiro-[cyclopentane-1,2'-(1'H)-naphthalen]-4'(3'H)-one A solution of 1.055 g 8'-hydroxy-spiro[cyclopentan-1,2'(1'H)-naphthalen]-4'(3'H)-one is added to a suspension of 218 mg sodium hydride (55% dispersion) in 20 ml N,N-dimethylformamide at room temperature and with stirring. The mixture is stirred for 2 hours at room temperature. A solution of 1.6 g (5S)-3-tert-butyl-5-tosyloxymethyl-2-oxazolidinone in 20 ml N,N-dimethylformamide is then added dropwise at room temperature and with stirring and the mixture stirred at 60° for 16 hours, then concentrated, diluted with water and extracted with methylene chloride. After evaporation of the solvent (5S)-3-tert-butyl-5-{3',4'-dihydro-4-oxospiro[cyclopentan-1,2'(1'H)-naphthalen]-8'-yloxymethyl}-2-oxazolidinone is obtained.

1.8 g of this crude product dissolved in 50 ml n-butanol is refluxed for 16 hours with 1.8 g sodium hydroxide, the solvent is then evaporated and the residue shaken with a mixture of NaCl-solution and ether. After evaporation of the ether extract the title compound is obtained: M.P. of the L(+)-hydrogen tartrate: 193°–195° (from ethanol); $[\alpha]_D$ −3.0° (c=2.0 in methanol).

The compounds of formula I are useful because they possess pharmacological activity in animals. In particular, the compounds are particularly useful as inhibitors of mobilisation of animal energy reserves, induced by emotional stress, e.g. by catecholamine secretion.

For example, the compounds inhibit the increased free fatty acid concentration in the blood, and the lipolysis effect, induced by emotional stress, as indicated by an inhibition of glycerol release stimulated by isoproterenol in standard tests, e.g. as follows:

(i) In vitro

Isolated fat cells are obtained from dog subcutaneous tisue, and from rat and quinea pig epididymal fat pads, in accordance with the method of M. Rodbell [J.Biol. Chem. 239, 375–380 (1964)]. Cells from one of the animals are dispersed in Krebs phosphate buffer containing 4% bovine serum albumin. 1 ml aliquots of the cell suspension in plastic incubation flasks are treated with the test substance at from about 0.0003 to about 10 mg/liter, e.g. from about 0.01 to about 10 mg/liter or from about 0.0003 to about 0.03 mg/liter, and isoproterenol at 10$^{-7}$ Molar. The glycerol release is determined in conventional manner, e.g. according to the method of S. Laurell et al., Helv. Chim. Acta 13, 317–322 (1966).

(ii) In vivo

Rats are fasted for 16 hours. A sub-cutaneous injection of 400 μg/kg of isoproterenol results in a glycerol concentration in the blood plasma of 400% the original value. This increased glycerol concentration remains constant for ca. 60 minutes and acts as a control value. The test substance is administered s.c. at a dose of from about 0.01 to about 0.5 mg/kg 10 minutes before the isoproterenol injection, and the animals are decapitated 40 minutes after the isoproterenol injection. The glycerol concentration in the blood is calculated in conventional manner, e.g. using the conventional glycero-3-phosphate-dehydrogenase method [according S. Laurell et al.; reference as mentioned above].

By virtue of their effect in reducing the increases in free fatty acid concentration in blood plasma, the compounds are therefore useful in the treatment of acut myocardial infarction in animals, resulting inter alia in a decrease in the risk of ventricular arrhythmias and further myocardial ischemic injury.

As indicated by the above, the compounds are additionally useful in the prophylaxis of myocardism in animals suffering from a myocardial ischemic injury, e.g. due to arteriosclerosis in the heart coronary arteries. Administration of the compounds prevents inter alia an increase in the ischemic zone in the heart and the anaerobic metabolic condition of the heart.

The compounds of formula I additionally inhibit hyperglycemia induced by emotional stress, as indicated by an inhibition of glycogenolysis in standard tests, as follows:

In the above-mentioned rat in vivo test the glucose concentration in the blood is determined in conventional manner, e.g. using the ferricyanide method. In the control animals the glucose concentration doubles after 40 minutes after isoproterenol administration. The compounds are administered parenterally at a dose of from about 0.001 to about 5 mg/kg, e.g. from about 0.01 to about 5 mg/kg or from about 0.001 to about 0.5 mg/kg animal body weight.

By virtue of their effect in the above test the compounds are therefore further useful as suppressants of appetite, e.g. induced by emotional stress. Such stress conditions are well appreciated in the art, e.g. see M. Carruthers et al., in D. M. Burely et al.; New Perspectives in beta-blockade, Int. Symposium Scanticon, Aarhus, Denmark, p. 275, 1972, and may include emotional stresses associated with car driving, speaking in public, and preparing for parachuting.

In addition, the compounds are useful as cardiovascular β-adrenoceptor blocking agents, e.g. for the prophylaxis and therapy of coronary diseases, particularly in the treatment of Angina pectoris, in the hyperkinetic heart syndrome, acute cardiac infarct, and conditions resulting from mulscular hypertrophic subvalvular aortic stenosis, and as anti-arrhythmic agents, e.g. for the treatment of heart rhythm disorders, as indicated in standard tests, e.g. by an inhibition of the positive inotropic adrenaline effect in the spontaneously beating quinea pig atrium at bath concentrations of from about 0.0016 to about 2.5 mg/liter, e.g. from about 0.005 to 2.5 mg/liter or from about 0.0016 to about 0.04 mg/liter in accordance with the method of K. Sammeli, Helv. Physiol. Acta 25, CR 215–221 (1967); and in the infusion test in narcotized cats at doses of approximately 0.02 to 0.6 mg/kg i.v., where they induce a strong, long lasting inhibition of the tachycardia and blood pressure lowering caused by isoproterenol.

The compounds are thus also useful for the prophylaxis and therapy of migraine, of conditions associated with sympathetic overstimulation, e.g. nervous heart ailments, and for the treatment of glaucoma and thyreotoxicosis.

In general, the 2(S) optical isomers are more active than the 2(R) optical isomers in the cardiovascular β-blocking tests.

For the above-mentioned uses the dosage will, of course, vary depending on the compound employed, mode of administration and treatment desired. However, in general, satisfactory results are obtained with a daily dosage of from about 0.001 to about 5 mg/kg animal body weight, conveniently given in divided doses 2 to 4 times a day or in sustained release form. For the larger mammal, the total daily dosage is in the range of from about 0.1 to about 200 mg, e.g. from about 1 to about 200 mg or about 0.1 to about 100 mg, and dosage forms suitable for oral or parenteral administration comprise from about 0.025 to about 100 mg, e.g. from about 0.25 to about 100 mg or about 0.025 to about 50 mg of the compounds admixed with a solid or liquid pharmaceutical carrier or diluent.

The comounds of formula I also exhibit a salidiuretic effect as indicated in standard tests, e.g. in the diuretic rat test in accordance with the principles of E. Flückiger et al., Schweiz. med. Wschr. 1963, 93 1232, on administration p.o. of from about 0.1 to about 50 mg/kg animal body weight of the compounds.

The compounds are therefore useful as salidiuretic agents, e.g. for the treatment of odema and hypertension.

For this use the dosage will, of course, vary depending on the compound employed, mode of administration and treatment desired. However, in general, satisfactory results are obtained when administered at a daily dosage of from about 0.1 mg to about 10 mg per kg animal body weight, conveniently given in divided doses 2 to 4 times a day of in sustained release form. For the larger mammal, the total daily dosage is in the range from about 1 to about 50 mg, and dosage forms suitable for oral administration comprise from about 0.25 mg to about 25 mg (e.g. 0.25 to 20 mg) of the compounds admixed with a solid or liquid pharmaceutical carrier or diluent.

The compounds of examples 1 and 2 have been found to be useful in the treatment of coronary disorders as indicated above in animals on administration of from 0.1 to 50 mg/kg animal body weight per day.

The example 1 and 2 compounds and especially the example 17 compound, exhibit particularly interesting properties.

The compounds may be administered in pharmaceutically acceptable acid addition salt form. Such forms exhibit the same order of activity as the free base forms. The present invention also provides a pharmaceutical composition comprising a compound of formula I in free base form or in pharmaceutically acceptable acid addition salt form, in association with a pharmaceutical carrier or diluent. Such compositions may be formulated in conventional manner so as to be, for example, a solution or tablet.

In a group of compounds p is 0, m is 1 and n is 1 or 2. Preferably $R_1$ is alkyl and $R_2$ and $R_3$ are each alkyl or together alkylene of 4 or 5 carbon atoms. In a sub-group $R_2$ and $R_3$ are together alkylene. In another sub-group $R_2$ is alkyl of 2 or 4 carbon atoms. In another group of compounds p is 1, m is 1 and n is 1. In another group p is 1, m is 0 and n is 1. In another group p is 1, m is 0 and n is 2.

We claim:
1. A compound of formula I

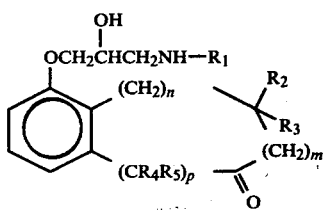

wherein
(i) m is 0, n is 2 and p is 1 or
(ii) m is 0 or 1, n is 1, and p is 1 or
(iii) m is 1, n is 1 or 2 and p is 0,
$R_1$ is (i) alkyl of 3 to 7 carbon atoms or (ii) phenylalkyl, phenoxyalkyl or phenylthioalkyl of 8 to 11 carbon atoms in the aggregate thereof and wherein the phenyl ring is separated by at least 2 carbon atoms from the nitrogen atom to which $R_1$ is bound and wherein the phenyl ring is unsubstituted, or mono-substituted by, or independently disubstituted by, alkyl or alkoxy of 1 to 4 carbon atoms, halogen of atomic number from 9 to 35, trifluoromethyl or cyano,
$R_2$ and $R_3$ are together straight chain alkylene of 4 to 6 carbon atoms, and
$R_4$ and $R_5$ are the same and are hydrogen or alkyl of 1 to 4 carbon atoms,
or a pharmaceutically acceptable acid addition salt thereof.

2. A process for the production of a compound of claim 1 which comprises reacting a compound of formula II

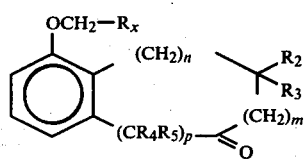

wherein
m, n, p and $R_2$ to $R_5$ are as defined above, and
$R_x$ is a group capable of reacting with an amine to give a 2-amino-1-hydroxyethyl group,
with a compound of formula III $R_1NH_2$     III wherein $R_1$ is defined above.

3. A pharmaceutical composition which comprises a therapeutically effective amount of a compound of claim 1 in association with a pharmaceutical carrier or diluent.

4. A method for treating coronary disorders, hypertension or odemas in animals which comprises administering a therapeutically effective amount of a compound of claim 1 to an animal in need of such treatment.

5. A method of treating, or preventing the further development of, a coronary disorder selected from arterial hypertension; acute cardiac infarct; myocardial infarction; and hyperlipidemia and hyperglycemia and increased appetite induced by emotional stress, which comprises administering a therapeutically effective amount of a compound of claim 1 to an animal in need of such treatment.

6. A compound of claim 1 which is 8'-(3-tert-butylamino-2-hydroxypropoxy)spiro[cyclopentane-1,2'(1'H)-naphthalen]-4'(3'H)-one.

7. A compound of claim 1 in individual optical isomer form.

8. A compound of claim 7 having the S configuration at the asymmetrically substituted carbon atom of the hydroxypropoxy side chain to which the hydroxy group is bound.

9. A compound of claim 8 which is 8'-[(2S)-3-tert-butylamino-2-hydroxypropoxy]spiro-[cyclopentane-1,2'-(1'H)-naphthalen]-4'(3'H)-one.

10. The compound of claim 1 in which m, n and p are 1, 1 and 0, respectively, $R_1$ is $-C(CH_3)_3$ and $R_2$ and $R_3$ together is $-(CH_2)_5$.

* * * * *